United States Patent

Brown et al.

(10) Patent No.: US 7,834,229 B2
(45) Date of Patent: Nov. 16, 2010

(54) OLEFIN OLIGOMERIZATION PROCESS

(75) Inventors: Stephen Harold Brown, Bernardsville, NJ (US); John Stephen Godsmark, Grez Doiceau (BE); Georges Marie Karel Mathys, Bierbeek (BE)

(73) Assignee: ExxonMobil Chemical Patents Inc., Houston, TX (US)

( * ) Notice: Subject to any disclaimer, the term of this patent is extended or adjusted under 35 U.S.C. 154(b) by 855 days.

(21) Appl. No.: 11/596,168

(22) PCT Filed: May 26, 2005

(86) PCT No.: PCT/EP2005/005785

§ 371 (c)(1),
(2), (4) Date: Nov. 10, 2006

(87) PCT Pub. No.: WO2005/118512

PCT Pub. Date: Dec. 15, 2005

(65) Prior Publication Data

US 2008/0039669 A1 Feb. 14, 2008

(30) Foreign Application Priority Data

Jun. 1, 2004 (GB) ................. 0412139.8

(51) Int. Cl.
*C07C 2/10* (2006.01)
*C07C 2/24* (2006.01)
(52) U.S. Cl. .............. 585/533; 585/514; 585/527
(58) Field of Classification Search ............... None
See application file for complete search history.

(56) References Cited

U.S. PATENT DOCUMENTS

| | | | |
|---|---|---|---|
| 3,960,978 A | 6/1976 | Givens et al. | 260/683.15 R |
| 4,021,502 A | 5/1977 | Plank et al. | 260/683.15 R |
| 4,520,221 A | 5/1985 | Hsia Chen | 585/517 |
| 4,675,463 A | 6/1987 | Glivicky et al. | 585/820 |
| 4,919,896 A | 4/1990 | Harandi et al. | 422/142 |
| 5,157,201 A | 10/1992 | Norris | |
| 5,672,800 A | 9/1997 | Mathys et al. | 585/520 |
| 6,025,533 A | 2/2000 | Vora et al. | 585/330 |
| 6,143,942 A * | 11/2000 | Verrelst et al. | 585/533 |
| 2002/0111523 A1* | 8/2002 | Mathys et al. | 585/518 |
| 2007/0173676 A1 | 7/2007 | Brown et al. | |

FOREIGN PATENT DOCUMENTS

| | | |
|---|---|---|
| EP | 0 746 538 | 12/1996 |
| WO | WO 94/12452 | 6/1994 |
| WO | WO 95/22516 | 8/1995 |
| WO | WO 03/035583 | 5/2003 |
| WO | WO 03/035584 | 5/2003 |
| WO | WO 2005/118513 | 12/2005 |

OTHER PUBLICATIONS

U.S. Appl. No. 11/596,170 Notice of Allowance dated Mar. 23, 2010.

* cited by examiner

*Primary Examiner*—In Suk Bullock
(74) *Attorney, Agent, or Firm*—Andrew B. Griffis; Leandro Arechederra, III

(57) ABSTRACT

In a process for oligomerizing an olefinic hydrocarbon feedstock comprising at least 65 wt % olefins and/or sulfur-containing molecules, the feedstock is contacted under oligomerization conditions with (a) a first unidimensional 10-ring molecular sieve catalyst and (b) a second multidimensional crystalline molecular sieve catalyst. The first and second catalysts may be contained in separate reactors or as separate beds in a single reactor.

44 Claims, 1 Drawing Sheet

OLEFIN OLIGOMERIZATION PROCESS

CROSS REFERENCE TO RELATED APPLICATIONS

This application is a National Stage Application of International Application No. PCT/EP2005/005785, filed May 26, 2005 and claims priority to GB Patent Application No. 0412139.8 filed Jun. 1, 2004. This application is also related by subject matter to GB Patent Application 0412151.3 filed 1 Jun. 2004 and its equivalent PCT patent application, the disclosures of which are incorporated by reference.

FIELD

The present invention relates to a process for the oligomerization of olefin containing feedstocks, particularly feedstocks containing at least about 65 wt. % olefins, and more particularly but not exclusively sulfur containing feedstocks.

BACKGROUND

The oligomerization of lower olefins, particularly $C_2$ to $C_6$ olefins, to produce higher molecular weight olefinic products is an important commercial process useful in, for example, the production of fuels and precursors for plasticizers, surfactants, and freeze point depressants for lubricating oils.

For example, approximately 70 units exist world wide for the purpose of oligomerizing olefins (typically mixtures of propylene and butenes) e.g. from Fluid Catalytic Cracker (FCC) unsaturated gas plants and/or steam crackers to gasoline and or distillate. These plants employ multiple reactors filled with solid phosphoric acid catalyst (sPa). SPa catalyst typically produces 500 to 1500 weight units of oligomer per weight unit of catalyst and then reaches the end of its useful life. As a result, most operators are required to shut down and reload catalyst into a reactor every 3 to 10 weeks. The reactor is taken off line, refilled with fresh catalyst, and brought back on line. Reactor turnaround for sPa catalyst is particularly difficult. During the course of use, sPa catalyst agglomerates to form a single, solid block which must be water jetted or drilled out of the reactor. Although sPa catalyst is inexpensive (currently about $2/lb), catalyst cost to produce oligomer is high compared to processes with more productive catalysts such as hydrotreating catalysts, hydrocracking catalysts, FCC catalysts, ethylbenzene and cumene catalysts, xylene isomerization catalysts, etc. due to the large quantities of sPa catalyst required and the expense associated with shutting down and restarting reactors.

For many units, sPa catalyst useful lifetime is limited by the increasing pressure drop caused by the steady catalyst agglomeration and not by loss of too much catalyst activity. Because of these problems, operators of sPa olefin oligomerization units are careful to maintain operating conditions that maximize catalyst cycle length. The rate of sPa fouling is known to increase with increasing feed olefin concentration. Many sPa operators therefore dilute the olefin feedstock with a paraffin recycle to increase catalyst lifetime. Paraffin dilution decreases the capacity of the unit by taking up space in pumps, reactors, heat exchangers and distillation towers.

One example of a process that utilizes a solid phosphoric acid oligomerization catalyst is U.S. Pat. No. 6,025,533, which describes a process for the production of heavy oligomers by a combination of dehydrogenation and oligomerization.

It is also known that zeolites can be attractive replacements for sPa catalysts because of their unique selectivities in olefin oligomerization. In addition, zeolite catalysts in light olefin oligomerization service do not swell and fuse, and the pressure drop across the unit remains small and constant throughout the full catalyst cycle. Zeolite catalyst fouling is also typically independent of feed olefin concentration.

For example, U.S. Pat. Nos. 3,960,978 and 4,021,502 disclose the conversion of gaseous olefins in the range of ethylene to pentene, either alone or in admixture with paraffins, into an olefinic gasoline blending stock by contacting the olefins with a ZSM-5 type zeolite. In addition, EP-B-746,538 discloses oligomerization of propene and butene to produce enhanced yields of the trimer using zeolites of the structure types MFI, TON, and MFS, such as ZSM-5, ZSM-22 and ZSM-57.

International Patent Publication No. WO 94/12452, published Jun. 9, 1994, discloses a process for producing a branched $C_4$-$C_5$ olefin by contacting a mixture of ethylene and a $C_3$-$C_{10}$ olefin with a molecular sieve selected from ZSM-22, ZSM-23, ZSM-35, ZSM-50 and SAPO-11 at a temperature of 200-700° C.

U.S. Pat. No. 4,919,896 describes the use of series reactors for oligomerization of olefins; a number of different zeolites, including ZSM-22, are proposed as catalysts.

U.S. Pat. No. 5,672,800 describes a process for oligomerization of $C_2$-$C_{12}$ alkene-containing feedstock having a water content of from 0.05 to 0.25 molar % over a zeolite catalyst.

U.S. Pat. No. 6,143,942 and International Patent Publication No. WO 95/22516, published Aug. 24, 1995, disclose an olefin oligomerization process comprising contacting a feed comprising at least one olefin under oligomerization conditions with a catalyst comprising at least one zeolite having a constraint index greater than 10, such as ZSM-22, and at least one zeolite having a constraint index of 2 to 10, such as ZSM-5 or ZSM-57, said zeolites being present in a proportion within the range of 10:90 to 90:10 by weight. Advantageously the two molecular sieves are in admixture but they can also be arranged in separate beds so that the feed passes through them in series. The feed can contain an inert diluent, such as a saturated hydrocarbon, in addition to said at least one olefin. For a feed comprising propene, a suitable diluent is said to be propane, advantageously in proportions of propene:propane from 10:90 to 60:40, especially about 50:50 by weight.

Among the most selective zeolites for the production of dimers and trimers in olefin oligomerization is ZSM-57 and other molecular sieves having pores defined by multidimensional channels of formed by 8-, 10-, and 12-membered rings of tetrahedrally coordinated atoms. However, it has been found that these materials can pose problems when used to oligomerize olefins under commercial, non-isothermal conditions.

Thus high-olefin content (>65%) feedstocks containing propylene are among the most important feedstocks in the industry but oligomerization of these feedstocks is highly exothermic. Hence, when ZSM-57 and similar multidimensional zeolite catalysts are used to process such feedstocks, large and unstable exotherms can develop anywhere in the reactor bed requiring reactor shutdown. Moreover, it has been found that the performance of these molecular sieves is negatively affected by the sulfur present in commercially available olefinic feedstocks. Although the reason for these observations is not fully understood, it is believed that the presence of certain sulfur compounds can result in a rapid decrease in activity, selectivity, and stability of the catalyst. In particular, it is believed that low molecular weight, aliphatic thiols, sulfides and disulfides are especially troublesome, for example dimethyl, diethyl, and ethyl methyl sulfides, n-propane thiol, 1-butane thiol and 1,1-methylethyl thiol, ethylmethyl and dimethyl disulfides, and tetrahydrothiophene.

There is therefore a need for an oligomerization process in which catalyst performance can be improved even with sulfur-containing feedstocks.

There is also therefore a need for an oligomerization process in which catalyst lifetime can be improved and in which high olefin content feedstocks can be processed without the production of large or uncontrollable exotherms.

SUMMARY

Accordingly, the invention resides in one aspect in a process for oligomerizing an olefinic hydrocarbon feedstock comprising at least about 65 wt. % olefins, the process comprising:

(a) contacting the feedstock with a catalyst comprising a crystalline molecular sieve having pores defined by unidimensional channels formed by 10-membered rings of tetrahedrally coordinated atoms, and (b) contacting the feedstock under olefin oligomerization conditions with a catalyst comprising a crystalline molecular sieve having pores defined by multidimensional channels.

Conveniently, the hydrocarbon feedstock comprises at least about 70 wt. % olefins, such as at least about 75 wt. % olefins.

In another aspect, the invention resides in a process for oligomerizing an olefinic hydrocarbon feedstock comprising sulfur-containing molecules, the process comprising:

(a) contacting the feedstock under olefin oligomerization conditions with a catalyst comprising a crystalline molecular sieve having pores defined by unidimensional channels formed by 10-membered rings of tetrahedrally coordinated atoms, and (b) contacting the feedstock under olefin oligomerization conditions with a catalyst comprising a crystalline molecular sieve having pores defined by multidimensional channels.

It will be understood for both aspects of the invention that, since the contacting steps (a), and (b) are performed sequentially (preferably with (a) first, but possibly with (b) first), the 'feedstock' that contacts catalyst in the second step will in fact be the initial feedstock that has already been contacted under oligomerization conditions with catalyst in the first step. Conveniently the feedstock comprises at least one olefin having about 2 to about 12 carbon atoms, preferably 2 to 6 carbon atoms such as propylene and/or butene.

Conveniently the feedstock comprises at least one olefin having about 2 to about 12 carbon atoms, preferably 2 to 6 carbon atoms, such as propylene and/or butene. In one embodiment, the hydrocarbon feedstock comprises about 0.1 to about 10,000 ppm, such as about 1 to about 100 ppm, by volume of sulfur-containing molecules.

The sulfur-containing molecules may, for example, be selected from methyl mercaptan, ethyl mercaptan, propyl mercaptan, dimethyl sulfide, diethyl sulfide, ethyl methyl sulfide, n-propyl sulfide, 1- and 2-propane thiol, 1-butane thiol and 1,1-methylethyl thiol, ethylmethyl disulfide, dimethyl disulfide and tetrahydrothiophene.

Conveniently, the crystalline molecular sieve of the first catalyst has the TON structure type.

Conveniently, the crystalline molecular sieve of the second catalyst has the MFS structure type.

Conveniently, the feedstock is hydrated prior to contact with the crystalline molecular sieve catalyst.

DETAILED DESCRIPTION OF THE EMBODIMENTS

Figure 1:
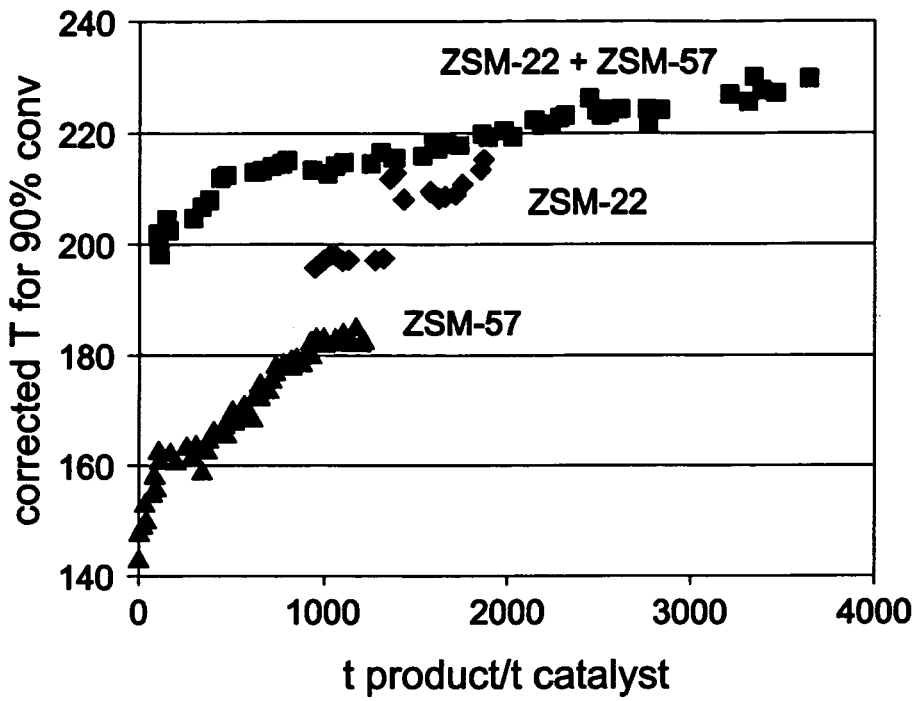
FIG. 1 is a graph showing the deactivation rate for a ZSM-57 catalyst used in the oligomerization of propylene both with and without prior contacting with a ZSM-22 oligomerization catalyst.

The present invention provides a process for oligomerizing an olefinic hydrocarbon feedstock, and in particular a feedstock containing at least 65 wt. % olefins and/or sulfur impurities, in which the feedstock is contacted under oligomerization conditions with (a) a first oligomerization catalyst comprising a crystalline molecular sieve having pores defined by unidimensional channels formed by 10-membered rings of tetrahedrally coordinated atoms and (b) a second oligomerization catalyst comprising a crystalline molecular sieve having pores defined by multidimensional channels. Such multidimensional rings are for example those normally formed by 10-membered or 12-membered rings of tetrahedrally coordinated atoms.

In a modification of the invention, which may be employed when particular tailoring of the product is required, after contact steps (a) and (b) have been carried out, the oligomerized product from the second of (a) and (b) is contacted under oligomerization conditions with (c) an oligomerization catalyst comprising solid phosphoric acid (sPa). This modification takes advantage of the particular catalytic characteristics of sPa for the (oligomer-rich) feedstock, while at the same time taking advantage of the catalytic characteristics of the unidimensional-channel and multidimensional-channel molecular sieves as described. Moreover, it enables low proportions of sPa to be used, thereby minimizing the handling and disposal problems typically associated with sPa.

In one embodiment, the catalysts employed in said contacting (a) and said contacting (b) comprise stacked beds in a single reactor. In another embodiment, the catalysts employed in said contacting (a) and said contacting (b) are contained in separate reactors.

Conveniently, the hydrocarbon feedstock is contacted first with the unidimensional 10-ring molecular sieve catalyst prior to contacting with the multidimensional crystalline molecular sieve catalyst, that is, step (a) is effected before step (b). In conventional reactor arrangements, this means that the unidimensional 10-ring molecular sieve catalyst is on top of the multidimensional molecular sieve catalyst. Thus, although multidimensional sieves, for example 10-ring and 12-ring molecular sieves, particularly ZSM-57, are highly selective for the production of dimers and trimers in the oligomerization of olefins such as propylene and butenes, they are sensitive to the presence of sulfur impurities in the feed and excessive exotherms can result if the olefin content is too high (>65%). In contrast, unidimensional 10-ring molecular sieves, such as ZSM-22 are less sensitive to sulfur impurities and tend to restrict oligomerization at the dimer stage, thereby limiting the amount of exotherm that occurs, especially with high olefin content feeds.

In addition, placing the less active unidimensional channel catalyst e.g. ZSM-22 on top of the multidimensional channel catalyst e.g. ZSM-57 helps maintain an isothermal reactor profile in a tubular reactor. Using a single bed of ZSM-57 or ZSM-22 catalyst results in a significant amount of extra heat being released at the top of a tubular reactor operating to effect olefins conversion at commercially useful >90% per pass conversion. The extra heat is released at the top of the reactor because the reaction driving force is much higher there (monomer concentration is highest at the top of the tube). Providing the more active catalyst at the bottom of the reactor tube helps shift heat release from the top to the bottom of the reactor allowing more isothermal operation. This helps optimize catalyst stability and selectivity.

Feedstock

The hydrocarbon feedstock used in the present process typically contains olefins having from about 2 to about 12 carbon atoms, such as from about 2 to about 6 carbon atoms. The feedstock itself may be or comprise an oligomer, such as a dimer, especially one provided by recycling a part of a product stream. In one embodiment, the feed contains propene, butenes, pentenes and/or hexenes. The process is especially applicable to propene and butene oligomerization.

The feedstock may contain greater than about 65 wt. % olefins, such as greater than about 70 wt. % olefins or greater than about 75 wt. % olefins.

Suitable feedstocks include untreated refinery streams such as FCC, coker, and pygas streams as well as aromatics-containing streams, such as reformates. One particularly preferred feedstock comprises an FCC light olefin stream, which typically comprises ethane, ethylene, propane, propylene, isobutane, n-butane, butenes and pentanes. An example of such a feedstock possesses the following composition:

|           | Wt. % | Mole % |
|-----------|-------|--------|
| Ethane    | 3.3   | 5.1    |
| Ethylene  | 0.7   | 1.2    |
| Propane   | 4.5   | 15.3   |
| Propylene | 42.5  | 46.8   |
| Isobutane | 12.9  | 10.3   |
| n-Butane  | 3.3   | 2.6    |
| Butenes   | 22.1  | 18.32  |
| Pentanes  | 0.7   | 0.4    |

In addition, the feedstock may comprise an inert diluent, for example, a saturated hydrocarbon.

As indicated above, the feedstock may also include sulfur-containing compounds, typically as impurities generated during production or separation of the feedstock. The feedstock may comprise from about 0.1 ppm to 10,000 ppm by volume of sulfur-containing compounds but more typically will contain from about 1 ppm to about 100 ppm, such as up to 50 ppm, for example up to 20 ppm by volume of such compounds. A typically encountered feedstock may have from 1 to 30 or from 2 to 20 ppm by volume of sulfur compounds, and the process is well suited to treating such feedstocks. The sulfur content is conveniently ascertained by gas chromatographic analysis using peak areas normalized with reference to a COS standard.

Examples of sulfur-containing compounds contained by the present feedstock include saturated aliphatic compounds, for example, thiols, sulfides, including cyclic sulfides, and disulfides. Typical compounds include, for example, methyl mercaptan, ethyl mercaptan, propyl mercaptan, dimethyl sulfide, diethyl sulfide, ethyl methyl sulfide, n-propyl sulfide, 1- and 2-propane thiol, 1-butane thiol and 1,1-methylethyl thiol, ethylmethyl disulphide, dimethyl disulfide and tetrahydrothiophene.

Prior to oligomerization, the feedstock may be hydrated and in particular sufficient water may be added to saturate the feedstock. Conveniently, the feedstock comprises from about 0.01 to about 0.25, such as from about 0.02 to about 0.20 and for example from about 0.03 to about 0.10, molar % water based on the total hydrocarbon content of the feedstock. If desired or required, the natural water content of the feedstock may be increased, for example, by passage through a thermostatted water saturator. Since the amount of water required to saturate the feedstock will depend upon the temperature and composition of the feedstock, control of the water content may be effected by appropriate control of the temperature of the feedstock.

Crystalline Molecular Sieve Oligomerization Catalysts

In the oligomerization process of the invention, the olefinic hydrocarbon feedstock is contacted, preferably initially, with a unidimensional 10-membered ring crystalline molecular sieve catalyst. The catalyst can include any unidimensional 10-membered ring crystalline molecular sieve that is active in olefin oligomerization reactions. Examples of suitable unidimensional 10-ring molecular sieves include those of the TON structure type (for example, ZSM-22, ISI-1, Theta-1, Nu-10, and KZ-2), those of the MEL-structure type (for example, ZSM-11), those of the EUO structure type (for example, EU-1 and ZSM-50), those of the AEL structure type (for example, SAPO-11), those of the MTT structure type (for example, ZSM-23 and KZ-1) and members of the ZSM-48 family of molecular sieves (for example, ZSM-48 itself). In this specification, the term "structure type" is used in the sense described in the Structure Type Atlas, Zeolites 17, 1996. Preferably, the 10-ring molecular sieve used (preferably as the first catalyst) is ZSM-22, ZSM-23, or SAPO-11. The composition and manufacture of ZSM-22 are described in, for example, U.S. Pat. No. 4,556,477 and WO 93/25475. The composition and manufacture of ZSM-23 are described in, for example, U.S. Pat. No. 4,076,842. The composition and manufacture of SAPO-11 are described in, for example, U.S. Pat. Nos. 4,440,871 and 6,294,493.

In accordance with the invention, the olefinic hydrocarbon feedstock is also contacted (preferably as the second oligomerization catalyst) with a molecular sieve having pores defined by multidimensional channels. In particular, such catalyst preferably comprises a medium pore size molecular sieve having multidimensional channels formed by 10-membered or 12-membered rings of tetrahedrally coordinated atoms. The sieve preferably has a Constraint Index of about 1 to about 12. Constraint Index and a method of its determination are described in U.S. Pat. No. 4,016,218, which is incorporated herein by reference. Examples of suitable molecular sieves for use in the multidimensional sieve catalyst include those having the MFS structure type (for example, ZSM-57), those having the MFI structure type (for example, ZSM-5) and those having the FER structure type (for example, ZSM-35). Preferably, the molecular sieve employed in step (b), preferably as the second catalyst in the process, is ZSM-57, the composition and manufacture of which are described in, for example, EP-A-74,121 and U.S. Pat. No. 4,973,870.

Conveniently, the molecular sieves employed herein are in their H— or acid form. An as-synthesized molecular sieve is advantageously converted to its acid form by, for example acid treatment, e.g., by HCl, or by ammonium ion exchange, and subsequent calcination. The calcined materials may be post-treated, such as by steaming.

In addition, the molecular sieves employed herein conveniently have a crystallite size up to 5 μm, such as within the range of from 0.05 to 5 µm, for example from 0.05 to 2 µm, and typically from 0.1 to 1 µm.

Although the invention has been described with reference to aluminosilicate zeolites, it is possible to use, as is known in the art, a material in which silicon and aluminum have been replaced in whole or in part by other elements, silicon more especially by germanium or phosphorus and aluminum more especially by boron, gallium, chromium and iron, materials containing such replacement lattice elements also being termed zeolites, and the term being used in the broader sense in this specification.

The molecular sieve may be supported or unsupported, for example in powder form, or used as an extrudate with an appropriate binder. Where a binder is employed, the binder is preferably present in an amount such that the oligomerization catalyst contains between about 2 and about 80 wt % of the molecular sieve. The binder is conveniently a metal oxide, such as alumina In a preferred embodiment of the process of the present invention, the bottom of the light olefin oligomerization reactor (or downstream reactors in series configuration) is filled with the multidimensional 10-ring or 12-ring molecular sieve catalyst and the top of the reactor is filled with the unidimensional, 10-ring molecular sieve catalyst. With conventional downward flow, the unidimensional, 10-ring molecular sieve catalyst selectively converts the feedstock monomers to dimers before the feedstock contacts the multidimensional molecular sieve catalyst bed. The limited amount of heat released by the selective dimerization can be removed with conventional tubular or chamber reactors. Light olefin (C2-C7) concentration is lowered by the downstream multidimensional molecular sieve catalyst. Reduced light olefin, particularly propylene, feedstock is further converted to the desired distribution of higher oligomers over the downstream catalyst. Because the tendency to form uncontrollable exotherms is greatly reduced, feedstock with higher olefin concentration can be processed.

Oligomerization Reaction System

The unidimensional 10-membered ring molecular sieve catalyst may be provided in a separate bed or a separate reactor upstream of the multidimensional crystalline molecular sieve catalyst or may be provided as a top layer on the multidimensional molecular sieve oligomerization catalyst.

Conveniently, the reactor system comprises from about 10 to about 80 wt %, more preferably about 15 to about 60 wt %, of the unidimensional 10-membered ring molecular sieve based on the total weight of the unidimensional 10-membered ring molecular sieve and the multidimensional crystalline molecular sieve in the overall catalyst system.

Oligomerization Conditions

The reaction conditions used in the olefin oligomerization with the unidimensional 10-membered ring molecular sieve and with the multidimensional molecular sieve oligomerization catalysts are not narrowly defined and may be the same or different. However, preferred operating temperatures for the olefin oligomerization are generally between about 80° C. and about 350° C. Toward and above the upper end of the range, deoligomerization rates increase and may predominate over the oligomerization reaction, providing an upper limit to practical operation. More typically, the reaction temperature is in the range of about 130° C. to about 320° C., such as between about 135° C. and about 310° C., for example between about 160° C. and about 260° C.

The pressure is conveniently in the range of about 400 psig to about 4000 psig (2860 to 27680 Kpaa), such as from about 500 psig to about 1500 psig (3550 to 10440 kPaa). The olefin weight hourly space velocity is advantageously in the range of from about 0.1 hr$^{-1}$ to about 20 hr$^{-1}$, such as from about 0.5 hr$^{-1}$ to about 5 hr$^{-1}$.

In one preferred embodiment, at least one of (a) and (b) is conducted at conditions including a temperature ranging from 80° C. to 350° C.; an olefin weight hourly space velocity ranging from 0.1 hr$^{-1}$ to 20 hr$^{-1}$ and a pressure ranging from 2860 kPaa to 27680 kPaa.

In another preferred embodiment, at least one of (a) and (b) is conducted at conditions including a temperature ranging from 130° C. to 320° C.; a weight hourly space velocity ranging from 0.5 hr$^{-1}$ to 5 hr$^{-1}$ and a pressure ranging from 3550 kPaa to 10440 kPaa.

The invention will now be more particularly described with reference to the following Examples.

All of the examples are conducted in pilot units, with the liquid feedstock being fed to the units using displacement pumps controlled by, mass flow meters. The feedstock is saturated with water by passage upwardly through a vessel containing water at a constant temperature between 20 and 40° C. After exiting the hydrator the feed is pre-heated to the heater temperature and then passed downwards through a fixed-bed reactor equipped with an internal thermowell. The oligomerization reaction is conducted at temperatures of 130 to 300° C. and a pressure of 70 bar (7000 kPa) to ensure single phase conditions. The reaction is exothermic leading to a non-isothermal temperature profile down the length of the catalyst bed.

Figure 2:
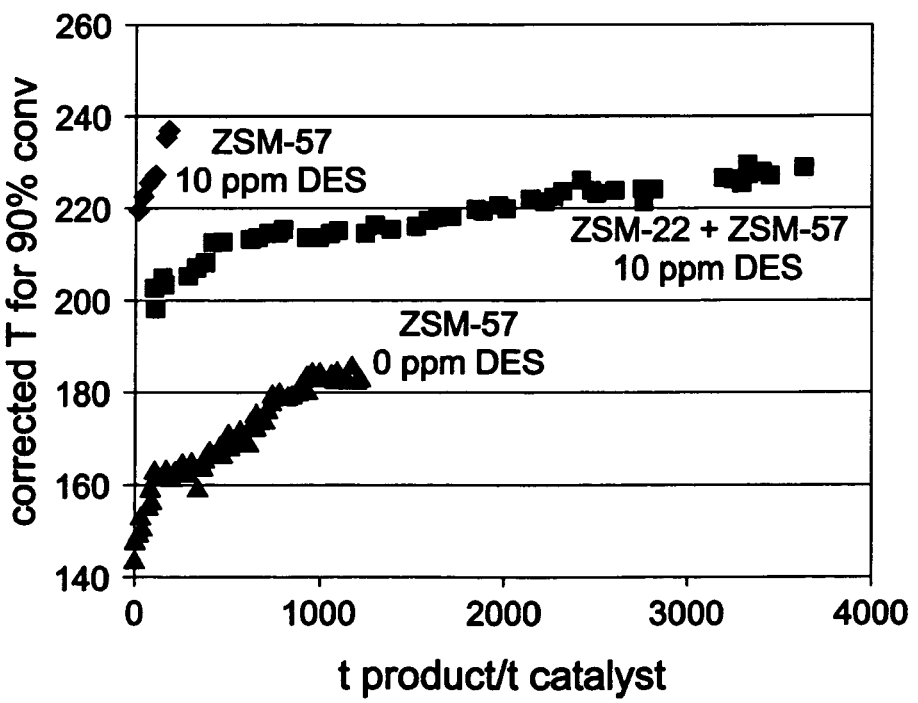
FIG. 2 is a graph showing the deactivation rate for a ZSM-57 catalyst used in the oligomerization of a propylene feedstock containing diethyl sulfide both with and without prior contacting with a ZSM-22 oligomerization catalyst.

No $C_2$-gases are fed or produced, and there is no evidence of any feedstock cracking. The product is cooled to near room temperature and the pressure is allowed to decrease to 20 bar (2000 kPa). Total reactor effluent samples are taken at 20 bar (2000 kPa) and are analyzed by GC. The feed and product olefin/paraffin ratios are compared in order to measure conversion. Liquid product is analyzed on a GC equipped with a platinum catalyst to hydrogenate product olefins to paraffins. Carbon number distribution and paraffin distribution are determined. Deactivation performance is shown in FIGS. 1 and 2.

The oligomerization catalysts, 50% ZSM-57/50% alumina extrudate catalyst and 75% ZSM-22/25% alumina extrudate catalyst, used in Examples 1 to 7 have the properties set forth in Table 1 below. The catalysts are in the activated hydrogen form.

TABLE 1

| | Catalyst | |
|---|---|---|
| | ZSM-22 | ZSM-57 |
| Zeolite Content | 75 | 50 |
| SiO2/Al2O3 | 65 | 40 |
| BET | 240 | 358 |
| n-hexane (mg/gm) | 39 | 50 |
| Alpha | 45 | 180 |
| Na (ppm) | 110 | <50 |
| K (ppm) | 700 | 110 |
| C (wt. %) | 0.35 | 0.2 |

Example 1

ZSM-57 with 75 wt. % Propylene Feedstock

ZSM-57/alumina extrudates are used to process 75 wt. % propylene/25 wt. % propane feedstock. Reaction conditions are 70 bar (7000 kPa), 2 WHSV and a furnace temperature of 130-150° C. Deactivation data are provided in FIG. 1 labeled ZSM-57. At the low end of the temperature range, propylene conversion is less than 40 wt. % and the reactor is nearly uniform in temperature from top to the bottom of the catalyst bed. Increasing temperature by as little as 2° C. causes conversion to increase to greater than 99% and temperatures approaching 300° C. are recorded at the top of the catalyst bed. Target conversion of 90% is not achievable.

Example 2

ZSM-57 with 50 wt. % Propylene Feedstock

ZSM-57/alumina extrudates are used to process 50 wt. % propylene/42 wt. % n-butane/8 wt. % isobutane feedstock. Reaction conditions are 70 bar (7000 kPa), 2-4 WHSV, 80-95% propylene conversion. Deactivation data are provided in FIG. 1 labeled ZSM-57.

Example 3

ZSM-22 with 75 wt. % Propylene Feedstock

ZSM-22/alumina extrudates are used to process 75 wt. % propylene/25 wt. % propane feedstock. Reaction conditions are 70 bar (7000 kPa), 3 WHSV, 50-98% propylene conversion. Deactivation data are provided in FIG. 1 labeled ZSM-22.

Example 4

ZSM-22 and ZSM-57 with 75 wt. % Propylene Feedstock

ZSM-22/alumina extrudates and ZSM-57/alumina extrudates are used to process 75 wt. % propylene/25 wt. % propane feedstock. The feedstock first contacts 66 wt. % ZSM-22 catalyst located in the upper portion of the reactor, then 34 wt. % ZSM-57 catalyst located in the lower portion of the reactor. [Total weight of ZSM-22 and ZSM-57 in the reactor corresponds to 100 wt %]. Reaction conditions are 70 bar (7000 kPa), 3 WHSV, 85-98% propylene conversion. Deactivation data are provided in FIG. 1 labeled ZSM-22+ZSM-57.

In reviewing FIG. 1, it is to be appreciated that light olefin oligomerization is typically conducted at a fixed feed rate and conversion. Freshly regenerated catalyst has the greatest activity. Because the desired feed rate is fixed, the reaction temperature is typically adjusted to maintain the target feedstock conversion. As the catalyst deactivates, the reaction temperature is raised to maintain constant conversion. This process is typically monitored by plotting the temperature required to achieve target conversion at the target WHSV against time. It is often desirable to track the stability of catalyst between and within runs where a variety of feed rates are utilized. To accomplish this, time is replaced by the cumulative amount of product produced by the catalyst expressed as weight units of product produced/wt unit of catalyst. In FIG. 1, the weight unit chosen is the ton, denoted as t in the drawing. The longer a reactor runs at constant conditions within the practical temperature range of the unit expressed either as days on stream or t product/t catalyst, the more stable the catalyst.

Example 2 shows that ZSM-57 can be used as an active and stable catalyst for the conversion of 50 wt. % propylene/50 wt. % butanes feedstock. Example 1 shows that increasing the propylene content of the feedstock to 75 wt. % can prevent the ability to operate. The conditions of Example 1 are representative of commercial operations and the catalyst of Example 1 cannot be used to commercially process 75 wt. % propylene feedstock using conventional tubular or chamber reactors. Example 3 shows that active and stable operation is possible with ZSM-22 catalyst during the processing of high concentration propylene feedstock. Example 4 shows that active and stable operation is possible with ZSM-22 catalyst on top of ZSM-57 catalyst during the processing of high concentration propylene feedstock.

Dimers are formed in the top of the reactor bed and undergo subsequent conversion to the desired product in the bottom of the catalyst bed. ZSM-22 allows processing of feeds rich in propylene because ZSM-22 is dimer selective. Example 4 shows that ZSM-22 can be used in combination with downstream multidimensional molecular sieves to allow stable operation with high olefin concentration feedstocks and maintain selectivity to higher oligomers versus dimers.

Example 5

ZSM-57 with Sulfur-Containing Feedstock

ZSM-57/alumina extrudates are used to process refinery propylene feedstock containing sulfur and oxygenate impurities having the composition as set forth in Table 2 below. Reaction conditions are 70 bar (7000 kPa), 2 WHSV, 80-95% propylene conversion. Deactivation data are shown in FIG. 2 labeled ZSM-57/10 ppm DES (diethyl sulfide).

TABLE 2

| Hydrocarbons, wt % | |
|---|---|
| ethane | 3.77 |
| ethene | 0.6 |
| propane | 18.54 |
| propene | 43.99 |
| iso-butane | 19.74 |
| n-butane | 10.72 |
| 1-butene | 0.36 |
| iso-butene | 0.62 |
| t-2-butene | 0.59 |
| c-2-butene | 0.35 |
| Oxygenates, wt ppm | |
| t-butyl alcohol | 8 |
| sec-butyl alcohol + methanol | 8 |
| iso-propyl alcohol | 97 |
| acetone | 135 |
| methyl ethyl ketone | 45 |
| Sulfur Compounds, wt ppm | |
| dimethyl sulfide | 0.6 |
| thiophene | 1 |
| propyl mercaptan | 1.3 |
| isobutyl mercaptan | 0.1 |
| diethyl sulfide | 6 |
| butyl mercaptan | 0.1 |
| dimethyl disulfide | 0.6 |
| tetrahydrothiophene | 1.1 |
| methylthiophenes | 0.8 |
| isopropyl sulfide | 1 |
| methyl ethyl sulfide | 0.3 |
| dimethyl thiophene | 0.3 |

Example 6

ZSM-57 with Sulfur Free Feedstock

ZSM-57/alumina extrudates are used to process 50 wt. % propylene/42 wt. % n-butane/8 wt. % isobutane feedstock. The feedstock contained no sulfur compounds. Reaction conditions are 2-4 WHSV, 70 bar (7000 kPa), 80-95% propylene conversion. Deactivation data are shown in FIG. 2 labeled ZSM-57/0 ppm DES.

Example 7

ZSM-22 and ZSM-57 with Sulfur-Containing Feedstock

ZSM-22/alumina extrudates and ZSM-57/alumina extrudates are used to process 75 wt. % propylene/25 wt. % propane feedstock spiked with 10 or 20 ppm DES. The top of the reactor is loaded with 66 wt. % ZSM-22 oligomerization catalyst and the bottom of the reactor is loaded with 34 wt. % ZSM-57 oligomerization catalyst. The feedstock is first contacted with the ZSM-22 oligomerization catalyst followed by the ZSM-57 oligomerization catalyst. Reaction conditions are 70 bar, 3 WHSV, 85-98% propylene conversion. Deactivation data are shown in FIG. 2 labeled ZSM-22+ZSM-57/10 ppm DES.

Comparing the results for Examples 5 and 6 in FIG. 2, it will be seen that the addition of 10 ppm DES to a clean propylene feedstock results in an 80° C. increase in the start of cycle temperature and rapid catalyst deactivation with a ZSM-57 catalyst. In contrast, the results obtained in Example 7 indicate that, using ZSM-22 followed by ZSM-57 with a propylene feedstock containing 10 ppm DES, results in significantly increased catalyst stability. In fact, although not shown in FIG. 2, ZSM-22 is less active than ZSM-57 and has a start cycle temperature of 190° C. for 90% conversion with a 75 wt. % propylene/25 wt. % propane feedstock. Thus it will be seen from FIG. 2 that the 200° C. start of cycle temperature obtained in Example 7 for the ZSM-22/ZSM-57 combination with a feed containing 10 ppm DES is relatively unchanged from the performance of ZSM-22 catalyst alone with a clean feed and that of ZSM-57 catalyst alone with the DES-containing feed.

While there have been described what are presently believed to be the preferred embodiments of the present invention, those skilled in the art will realize that other and further embodiments can be made without departing from the spirit of the invention, and is intended to include all such further modifications and changes as come within the true scope of the claims set forth herein.

The invention claimed is:

1. A process for oligomerizing an olefinic hydrocarbon feedstock comprising at least about 65 wt. % olefins and from about 3 ppm by volume to about 10,000 ppm by volume sulphur-containing compounds, the process comprising:
    (a) contacting the feedstock under olefin oligomerization conditions with a catalyst comprising a crystalline molecular sieve having pores defined by unidimensional channels formed by 10-membered rings of tetrahedrally coordinated atoms, and
    (b) contacting the feedstock under olefin oligomerization conditions with a catalyst comprising a crystalline molecular sieve having pores defined by multidimensional channels,
    wherein (a) is performed prior to (b).

2. The process of claim 1 wherein the crystalline molecular sieve in (a) comprises a TON material.

3. The process of claim 2 wherein the crystalline molecular sieve in (a) comprises ZSM-22.

4. The process of claim 1 wherein the crystalline molecular sieve in (a) comprises a MTT material.

5. The process of claim 4 wherein the crystalline molecular sieve in (a) comprises ZSM-23.

6. The process of claim 1 wherein the crystalline molecular sieve in (a) comprises a material selected from the group consisting of AEL materials and materials of the ZSM-48 family of molecular sieves.

7. The process of claim 6 wherein the crystalline molecular sieve in (a) comprises a material selected from the group consisting of SAPO-11 and ZSM-48.

8. The process of claim 1 wherein the crystalline molecular sieve in (b) has pores defined by multidimensional channels formed by rings selected from the group consisting of 10-membered and 12-membered rings of tetrahedrally coordinated atoms.

9. The process of claim 8 wherein the crystalline molecular sieve in (b) comprises a MFS material.

10. The process of claim 9 wherein the crystalline molecular sieve in (b) comprises ZSM-57.

11. The process of claim 1 wherein the hydrocarbon feedstock comprises at least about 70 wt. % olefins.

12. The process of claim 11 wherein the hydrocarbon feedstock comprises at least about 75 wt. % olefins.

13. The process of claim 1 wherein the hydrocarbon feedstock comprises at least one olefin having about 2 to about 12 carbon atoms.

14. The process of claim 13 wherein the hydrocarbon feedstock comprises at least one olefin having about 2 to about 6 carbon atoms.

15. The process of claim 14 wherein the hydrocarbon feedstock comprises at least one olefin selected from propylene, butenes and mixtures thereof.

16. The process of claim 1 wherein at least one of (a) and (b) is conducted at conditions including a temperature ranging from about 80° C. (176° F.) to about 350° C. (662° F.); an olefin weight hourly space velocity ranging from about 0.1 $hr^{-1}$ to about 20 $hr^{-1}$ and a pressure ranging from about 2,860 kPaa (400 psig) to about 27,680 kPaa (4000 psig).

17. The process of claim 1 wherein at least one of (a) and (b) is conducted at conditions including a temperature ranging from about 130° C. (266° F.) to about 320° C. (608° F.); a weight hourly space velocity ranging from about 0.5 $hr^{-1}$ to about 5 $hr^{-1}$ and a pressure ranging from about 3,550 kPaa (500 psig) to about 10,440 kPaa (1500 psig).

18. The process of claim 1 wherein the catalysts employed in said contacting (a) and said contacting (b) comprise stacked beds in a single reactor.

19. The process of claim 1 wherein the catalysts employed in said contacting (a) and said contacting (b) are contained in separate reactors.

20. A process for oligomerizing an olefinic hydrocarbon feedstock comprising from about 3 ppm by volume to about 10,000 ppm by volume sulphur-containing compounds, the process comprising:
    (a) contacting the feedstock under olefin oligomerization conditions with a catalyst comprising a crystalline molecular sieve having pores defined by unidimensional channels formed by 10-membered rings of tetrahedrally coordinated atoms, and
    (b) contacting the feedstock under olefin oligomerization conditions with a catalyst comprising a crystalline molecular sieve having pores defined by multidimensional channels,
    wherein (a) is performed prior to (b).

21. The process of claim 20 wherein the crystalline molecular sieve in (a) comprises a TON material.

22. The process of claim 21 wherein the crystalline molecular sieve in (a) comprises ZSM-22.

23. The process of claim 20 wherein the crystalline molecular sieve in (a) comprises a MTT material.

24. The process of claim 23 wherein the crystalline molecular sieve in (a) comprises ZSM-23.

25. The process of claim 20 wherein the crystalline molecular sieve in (a) comprises a material selected from the group consisting of AEL materials and materials of the ZSM-48 family of molecular sieves.

26. The process of claim 25 wherein the crystalline molecular sieve in (a) comprises a material selected from the group consisting of SAPO-11 and ZSM-48.

27. The process of claim 20 wherein the crystalline molecular sieve in (b) has pores defined by multidimensional channels formed by rings selected from the group consisting of 10-membered and 12-membered rings of tetrahedrally coordinated atoms.

28. The process of claim 27 wherein the crystalline molecular sieve in (b) comprises a MFS material.

29. The process of claim 28 wherein the crystalline molecular sieve in (b) comprises ZSM-57.

30. The process of claim 20 wherein the hydrocarbon feedstock comprises 3 to 20 ppm by volume of sulfur-containing compounds.

31. The process of claim 30 wherein the hydrocarbon feedstock comprises 10 to 20 ppm by volume of sulfur-containing compounds.

32. The process of claim 20 wherein the sulfur-containing compounds comprise at least one compound selected from the group consisting of methyl mercaptan, ethyl mercaptan, propyl mercaptan dimethyl sulfide, diethyl sulfide, ethyl methyl sulfide, n-propyl sulfide, 1-propane thiol, 2-propane thiol, 1-butane thiol, 1,1-methylethyl thiol, ethylmethyl disulfide, dimethyl disulfide, tetrahydrothiophene and mixtures thereof.

33. The process of claim 20 wherein the hydrocarbon feedstock comprises at least one olefin having about 2 to about 12 carbon atoms.

34. The process of claim 20 wherein the hydrocarbon feedstock comprises at least one olefin having about 2 to about 6 carbon atoms.

35. The process of claim 20 wherein the hydrocarbon feedstock comprises at least one olefin selected from propylene, butenes, and mixtures thereof.

36. The process of claim 20 wherein at least one of (a) and (b) is conducted at conditions including a temperature ranging from about 80° C. (176° F.) to about 350° C. (662° F.); an olefin weight hourly space velocity ranging from about 0.1 $hr^{-1}$ to about 20 $hr^{-1}$ and a pressure ranging from about 2,860 kPaa (400 psig) to about 27,680 kPaa (4000 psig).

37. The process of claim 20 wherein at least one of (a) and (b) is conducted at conditions including a temperature ranging from about 130° C. (266° F.) to about 320° C. (608° F.); a weight hourly space velocity ranging from about 0.5 $hr^{-1}$ to about 5 $hr^{-1}$ and a pressure ranging from about 3,550 kPaa (500 psig) to about 10,440 kPaa (1500 psig).

38. The process of claim 20 wherein the catalysts employed in said contacting (a) and said contacting (b) comprise stacked beds in a single reactor.

39. The process of claim 20 wherein the catalysts employed in said contacting (a) and said contacting (b) are contained in separate reactors.

40. The process of claim 20 wherein the hydrocarbon feedstock further comprises at least about 65 wt. % olefins.

41. The process of claim 40 wherein the hydrocarbon feedstock comprises at least about 70 wt. % olefins.

42. The process of claim 41 wherein the hydrocarbon feedstock comprises at least about 75 wt. % olefins.

43. The process of claim 1 wherein the sulphur-containing compounds consist essentially of diethyl sulfide (DES).

44. The process of claim 20 wherein the sulphur-containing compounds consist essentially of diethyl sulfide (DES).

* * * * *